United States Patent [19]

Berg

[11] Patent Number: 4,470,881
[45] Date of Patent: Sep. 11, 1984

[54] SEPARATION OF ETHYL ACETATE FROM METHYL ETHYL KETONE BY EXTRACTIVE DISTILLATION

[75] Inventor: Lloyd Berg, Bozeman, Mont.

[73] Assignee: Celanese Corporation, New York, N.Y.

[21] Appl. No.: 424,827

[22] Filed: Sep. 27, 1982

Related U.S. Application Data

[63] Continuation-in-part of Ser. No. 246,488, Mar. 23, 1981, abandoned, which is a continuation of Ser. No. 124,806, Feb. 25, 1980, abandoned.

[51] Int. Cl.³ .................... B01D 3/40; C07C 67/54; C07C 45/82
[52] U.S. Cl. .................................... 203/51; 203/56; 203/57; 203/58; 203/60; 203/61; 203/62; 203/63; 203/64; 203/65
[58] Field of Search .................... 203/56, 65, 60, 51, 203/DIG. 10, 61, 57, 58, 62, 63, 64, 66; 568/410; 560/248

[56] References Cited

U.S. PATENT DOCUMENTS

| | | | |
|---|---|---|---|
| 2,444,893 | 7/1948 | Lake | 203/44 |
| 2,862,853 | 12/1958 | Luke et al. | 203/83 |
| 3,228,985 | 1/1966 | Carpenter et al. | 568/410 |
| 3,591,463 | 7/1971 | Copelin | 568/410 |
| 3,691,021 | 9/1972 | Feldman et al. | 203/65 |
| 3,736,236 | 5/1973 | DiFiore et al. | 568/410 |

FOREIGN PATENT DOCUMENTS

| | | | |
|---|---|---|---|
| 115833 | 9/1980 | Japan | 560/248 |
| 765334 | 1/1957 | United Kingdom | 203/60 |

Primary Examiner—Wilbur L. Bascomb, Jr.
Attorney, Agent, or Firm—L. I. Grim; M. Turken

[57] ABSTRACT

A method for separating ethyl acetate from methyl ethyl ketone is described including distilling in an anhydrous condition a mixture of ethyl acetate-methyl ethyl ketone in a plate column in the presence of an effective amount of an organic extractive solvent which has the following properties: (1) is soluble in a boiling ethyl acetate-methyl ethyl ketone mixture; (2) does not form an azeotrope with ethyl acetate or methyl ethyl ketone; (3) boils higher than ethyl acetate and methyl ethyl ketone and (4) in combination with the ethyl acetate-methyl ethyl ketone mixture, results in a relative volatility of ethyl acetate to methyl ethyl ketone greater than 1.20.

8 Claims, 1 Drawing Figure

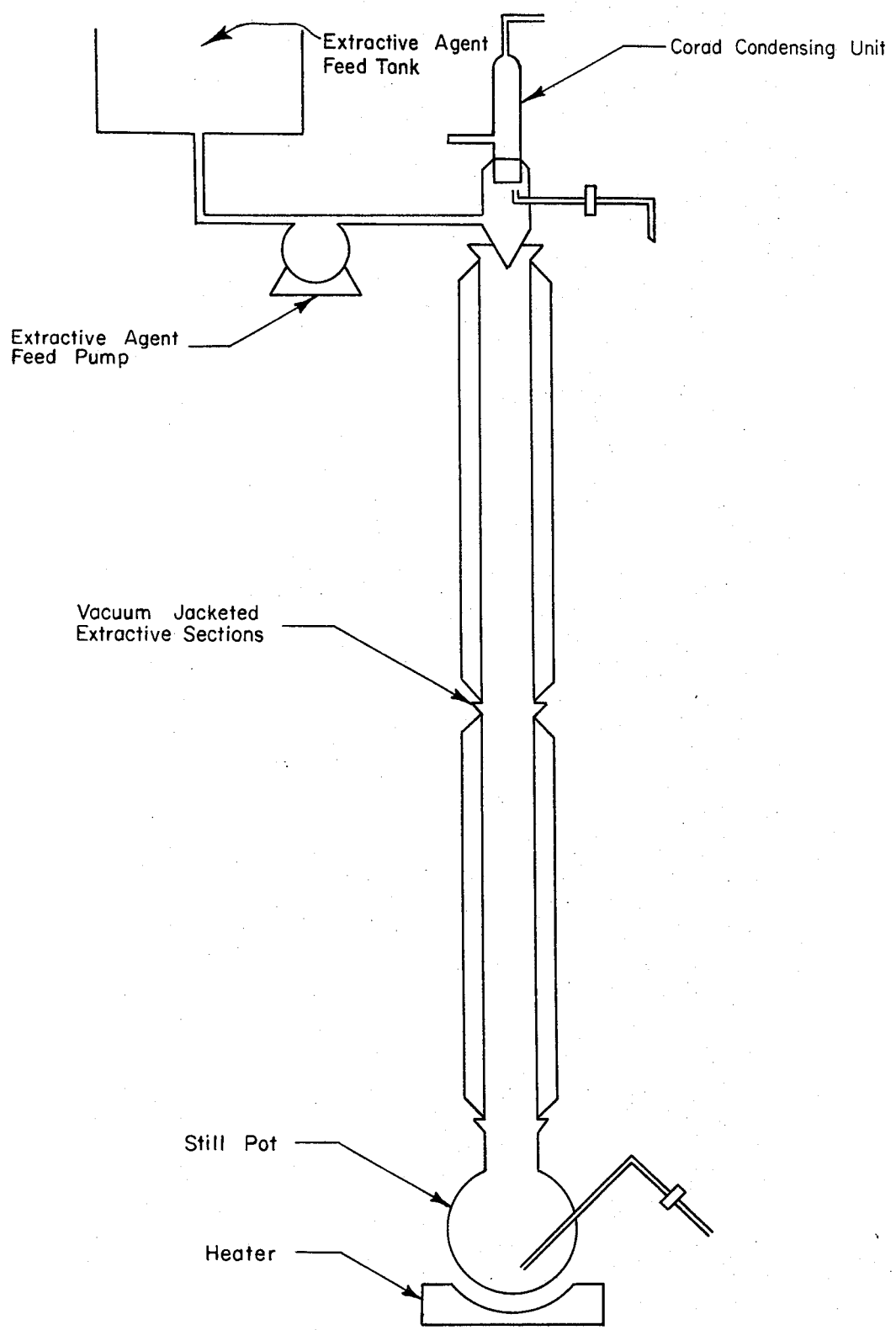

SEPARATION OF ETHYL ACETATE FROM METHYL ETHYL KETONE BY EXTRACTIVE DISTILLATION

This application is a continuation-in-part application of U.S. application Ser. No. 246,488 filed Mar. 23, 1981, now abandoned, which in turn is a continuation of U.S. application Ser. No. 124,806 filed Feb. 25, 1980, now abandoned.

This invention relates to an improved method for separating ethyl acetate from methyl ethyl ketone by extractive distillation.

BACKGROUND OF THE INVENTION

The separation of ethyl acetate from methyl ethyl ketone has heretofore presented considerable difficulty by reason of the fact that the boiling points of these two compounds is only 2.4° C. apart. This requires the use of fractionating columns containing a large number of plates and a high reflux ratio in order to obtain separation of these two compounds at an acceptable purity. Ethyl acetate and methyl ethyl ketone frequently occur together in manufacturing processes, thus posing an important separation problem. While separation is multiplate fractionating columns is the current preferred method, it is a costly step. For instance, to separate ethyl acetate from methyl ethyl ketone into two fractions each possessing a purity of 99%, it requires a column comprising a minimum of 118 theoretical plates.

A number of investigators have described methods for separating ethyl acetate from methyl ethyl ketone using azeotropic distillation. These include U.S. Pat. No. 2,703,783 to Harrison et al; U.S. Pat. No. 2,607,719 to Eliot et al and U.S. Pat. No. 2,528,761 to Lake et al.

U.S. Pat. No. 3,404,186 to Bailey et al describes the separation of methyl ethyl ketone (MEK) from ethyl acetate (EA) by hydrolyzing the methyl ethyl ketone-ethyl acetate fraction and recovering ethanol and methyl ethyl ketone. Water is added to the mixture and the methyl ethyl ketone is extracted with a hydrocarbon and the ethanol recovered in the water. U.S. Pat. No. 2,862,853 to Luke, Jr. et al describes an aqueous extractive distillation of methyl ethyl ketone and ethyl acetate fraction in a distillation of methyl ethyl ketone and ethyl acetate fraction in a distillation column. This procedure can be used to separate part of the ethyl acetate present from methyl ethyl ketone but will not provide a commercially pure methyl ethyl ketone, i.e., as high as 99% purity.

The presence of water will produce azeotropes with the ethyl acetate and methyl ethyl ketone in the ethyl acetate-methyl ethyl ketone mixtures which are extremely difficult to break and will not provide a substantial separation of the ethyl acetate from the methyl ethyl ketone.

THE INVENTION

An improved process has been discovered for separating ethyl acetate from methyl ethyl ketone by distillation in a substantially anhydrous condition in a rectifying plate column using extractive distillation with an organic solvent. The organic extractive solvent used in the process of this invention must have the following properties:

(1) the extractive solvent is soluble in boiling ethyl acetate-methyl ethyl ketone mixtures;

(2) the extractive solvent does not form an azeotrope with ethyl acetate, methyl ethyl ketone or combinations thereof;

(3) the extractive solvent boils higher than ethyl acetate and methyl ethyl ketone; and (4) the extractive solvent in combination with ethyl acetate and methyl ethyl ketone results in a relative volatility of ethyl acetate to methyl ethyl ketone greater than 1.20, preferably in the range from about 1.30 to about 1.50 and more preferably in the range from about 1.30 to 1.75.

Extractive distillation offers advantages in simplicity and efficiency over either conventional rectification or azeotropic distillation. The relative volatility of ethyl acetate (EA) to methyl ethyl ketone (MEK) is 1.08. When these two compounds are distilled in the presence of certain third components, the relative volatility of EA to MEK is increased. Selecting extractive distillation agents at random usually yields little or no improvement in relative volatility but if the right combinations are employed, a marked increase in relative volatility is observed and a corresponding large decrease in the number of theoretical plates required for separation are obtained. In view of this, extractive distillation can be considered as an alternative for the recovery of ethyl acetate and methyl ethyl ketone.

The types of distillation equipment which can be used in the process of this invention is the Oldershaw column containing plates as illustrated in the accompanying drawings or modifications thereof, an Othmer vapor-liquid equilibrium still and modifications thereof, other plate type columns such as feed trays or bubble plates, bubble cap units, reciprocating plate columns and the like.

To determine relative volatility for ethyl acetate to methyl ethyl ketone, the following formula is used:

$$\alpha = \frac{\text{mole fraction ethyl acetate vapor}}{\text{mole fraction ethyl acetate liquid}} \times \frac{\text{mole fraction methyl ethyl ketone liquid}}{\text{mole fraction methyl ethyl ketone vapor}}$$

$\alpha$ = relative volatility

= theoretical plates of distillation column

In the use of an Othmer vapor-liquid equilibrium still having one theoretical plate, the relative volatility of ethyl acetate to methyl ethyl ketone is determined as follows:

$$\text{relative volatility} = \frac{\text{mole fraction ethyl acetate vapor}}{\text{mole fraction ethyl acetate liquid}} \times \frac{\text{mole fraction methyl ethyl ketone liquid}}{\text{mole fraction methyl ethyl ketone vapor}}$$

The extractive solvents used in this invention can be a single compound or a mixture of two or more compounds and are used in proportion to provide the relative volatility greater than 1.2.

Single compounds suitable to be used as extractive solvents in the process of this invention include: maleic anhydride, isophorone, hexylene glycol, 2-4-pentanedione, diacetone alcohol, propylene glycol, catechol, m- and p-cresol, 2-naphthol, 1-naphthol, phenol, o-cresol and resorcinol. Compounds used in combination with phthalic anhydride as mixtures for extractive solvents for their use in the process of this invention include: maleic anhydride, isophorone and propylene glycol.

Compounds used in combination with maleic anhydride as mixtures for extractive solvents for their use in the process of this invention include: catechol, diacetone alcohol and propylene glycol. Other mixtures suitable for use in the process of this invention include: the mixtures of phthalic anhydride, maleic anhydride and compounds selected from a member of a group consisting of isophorone, diethyl maleate, the combination of diethylene glycol and dimethyl ether, isoborneol, dimethyl succinate, butoxypropanol, dibutyl phthalate, benzophenone, acetophenone, acetol, 2-octanone, diisobutyl ketone, methyl isoamyl ketone, diacetone alcohol, ethylene glycol stearate, benzyl alcohol, methyl-n-amyl ketone, phenethyl alcohol, benzyl benzoate, phenol, p-ethylbenzaldehyde, α-methyl benzyl alcohol, n-butanol, isobutanol, n-pentanol, 2-methyl-1-butanol, fenchyl alcohol, 3-methyl-1-butanol, 1-hexanol, cyclohexanol, isooctyl alcohol, nonyl alcohol, n-decanol, propionic anhydride, nitrobenzene, isobornyl acetate, 2-ethylbutanol, diisobutyl carbinol, acetonylacetone, ethylene glycol phenyl ether, phenyl acetic acid, ethylene glycol hexyl ether, hexylene glycol, propoxypropanol, 1,4-butanediol, propylene glycol, benzyl ether, benzil, 2,4-pentanedione, acetoin, diethyl carbonate, 2-methoxyethyl acetate, 2-nitropropane, 3-pentanone, 1,3-butylene glycol, 1,6-hexanediol, neopentyl glycol, dipropylene glycol, diethylene glycol, triethylene glycol, tripropylene glycol, glycerol, isodecanol, ethylene glycol and n-octanol.

Other mixtures which can be used as extractive solvents in the process of this invention include: 1-naphthol with each of the following: catechol, phenol, 4-t-butyl catechol, o-cresol, m-cresol, p-cresol, resorcinol, bis Phenol A, diphenyl ether, 2naphthol and pyrogallol. Other mixtures include: 4-t-butyl catechol and phenol; bis Phenol A and catechol; bis Phenol A and 2-naphthol; 2-naphthol and catechol; bis Phenol A and resorcinol; 2-naphthol and resorcinol; catechol and pyrogallol; pyrogallol and 2-naphthol; catechol and resorcinol; resorcinol with each individually o-cresol, m-cresol, and p-cresol; catechol and 2-t-butyl phenol; resorcinol and 3,5-dimethylphenol; resorcinol and 3,4-dimethylphenol; catechol and 3,4-dimethylphenol; catechol and 2,3-dimethylphenol; resorcinol and 2,3-dimethylphenol; catechol and 4-isopropylphenol; resorcinol and 2,3-dimethylphenol; catechol and 2-isopropylphenol; catechol and 4-t-butylcatechol; resorcinol and 4-t-butylcatechol; resorcinol and 2,6-dimethylphenol; catechol and 2,6-dimethylphenol; catechol and 2,6-dimethylphenol; catechol and 4-ethylphenol; catechol and 2-n-butyl-2-ethyl-1,3-propanediol; resorcinol and 2-n-butyl-2-ethyl-1,3-propanediol; resorcinol and 4-ethylphenol; catechol and phenol; resorcinol and phenol; hydroquinone, phenol and catechol; catechol and 4-nitrotoluene; hydroquinone, resorcinol and catechol; hydroquinone, resorcinol, catechol and 2-naphthol; hydroquinone, resorcinol, catechol and 2-naphthol; hydroquinone, resorcinol and 1-naphthol; catechol, resorcinol and 2-methyl-4-nitrophenol; catechol, resorcinol and pyrogallol; catechol and pyrogallol; catechol, resorcinol and 4-ethylphenol; hydroquinone, catechol, resorcinol and 4-ethylphenol; hydroquinone, catechol, resorcinol and pyrogallol; resorcinol and pyrogallol; catechol, resorcinol and o-sec butyl phenol or o-t-butyl phenol or 4-t-butyl phenol; catechol, resorcinol and 4-phenylphenol or 2-phenylphenol; m-p-cresol and catechol; m-p-cresol and resorcinol; resorcinol and 4-ethylphenol; hydroquinone, resorcinol, catechol and m-p-cresol or 4-ethylphenol or phenol or o-cresol; catechol and o-cresol; hydroquinone, o-cresol and m-p-cresol; hydroquinone and phenol; 2,5-di-t-butylhydroquinone and phenol; catechol and m-p-cresol; 4-t-butylphenol and m-p-cresol 4-t-butylcatechol and m-p-cresol; o-cresol and m-p-cresol; pyrogallol and m-p-cresol; m-p-cresol and o-sec-butylphenol or o-t-butylphenol; o-cresol and o-t-butylphenol; m-p-cresol and 4-ethylphenol; o-cresol and 4-ethylphenol; hydroquinone and m-p-cresol; hydroquinone and o-cresol; resorcinol and o-cresol; pyrogallol and o-cresol; o-sec butylphenol and o-cresol; hydroquinone, resorcinol; catechol and o-cresol; hydroquinone, resorcinol, catechol and pyrogallol; 2,5-di-t-butylhydroquinone, m-p-cresol and o-cresol; hydroquinone, resorcinol, catechol and pyrogallol, hydroquinone, catechol and pyrogallol; hydroquinone, resorcinol and pyrogallol; resorcinol, catechol and pyrogallol; catechol and hydroquinone, hydroquinone and pyragallol; hydroquinone and resorcinol; resorcinol and o-sec butylphenol; catechol and o-sec butylphenol; catechol and 4-t-amylphenol; catechol and 4-t-butylcatechol; hydroquinone, o-sec butylphenol and o-cresol; hydroquinone and catechol; hydroquinone, catechol and pyrogallol; catechol and toluhydroquinone; hydroquinone, toluhydroquinone and o-cresol; catechol and mono-t-butylhydroquinone; toluhydroquinone and mono-t-butylhydroquinone; toluhydroquinone and pyrogallol; mono-t-butylhydroquinone and pyrogallol; catechol and 4-nitrotoluene; catechol, 2,5-di-t-butylhydroquinone and o-cresol; hydroquinone and resorcinol; hydroquinone and hydroquinone monomethyl ether; catechol and hydroquinone monoethyl ether; resorcinol and hydroquinone monomethyl ether; catechol and hydroquinone di(β-hydroxyethyl)ether; resorcinol and hydroquinone di(β-hydroxyethyl)ether;hydroquinone, hydroquinone di(β-hydroxyethyl)ether and meta- and para-cresol; resorcinol, hydroquinone di(β-hydroxyethyl)ether and meta- and para-cresol; catechol and 1,4-dimethyoxybenzene; resorcinol and 1,4-dimethoxybenzene; catechol and p-hydroxyphenyl acetic acid; catechol and chlorohydroquinone; resorcinol and p-hydroxyphenyl acetic acid; 4,4'-sulfonyl diphenol and dimethylsulfoxide; dihydroxydiphenyl sulfone and dimethylsulfoxide, 4,4'-sulfonyl diphenol and dimethyl formamide; dihydroxydiphenol sulfone and dimethyl formamide; pentaerythritol and dimethylsulfoxide; 4-nitrophenol and meta- and para-cresol; 4-nitrolphenol and meta- and para-cresol; catechol and o-tertiary-butylphenol; catechol and p-cresol; catechol, hydroquinone and p-cresol; catechol, resorcinol and p-cresol; toluhydroquinone and p-cresol; toluhydroquinone, catechol and p-cresol; toluhydroquinone, resorcinol and p-cresol; toluhydroquinone, resorcinol and catechol; toluhydroquinone and resorcinol; phenol and p-cresol; toluhydroquinone, m-p-cresol, o-tertiary-butylphenol; o-sec butylphenol and p-cresol; phenol and 2-naphthol; catechol, hydroquinone and tetrahydrofurfuryl alcohol; catechol, resorcinol and tetrahydrofurfuryl alcohol; hydroquinone, resorcinol and tetrahydrofurfuryl alcohol, catechol, toluhydroquinone and tetrahydrofurfuryl alcohol; catechol, hydroquinone and benzl alcohol; catechol, resorcinol and benzyl alcohol; hydroquinone, resorcinol and benzyl alcohol; catechol, hydroquinone and ethyl acetoacetate; catechol, resorcinol and ethyl acetoacetate; hydroquinone, resorcinol and ethyl acetoacetate; hydroquinone, catechol and phenethyl alcohol; resorcinol, catechol and phenethyl alcohol; resorcinol, hydroquinone and phenethyl alcohol; catechol, hydroquinone and ethylphenyl acetate; catechol resorcinol and ethylphenyl acetate; hydroquinone, resorcinol and ethylphenyl acetate; toluhydroquinone, resorcinol and benzyl alcohol; toluhydroquinone, resorcinol and phenethyl alcohol; toluhydroquinone, resorcinol and ethylphenyl acetate; toluhydroquinone, resorcinol and diethyl maleate; toluhydroquinone, resorcinol and n-decanol; toluhydroquinone, resorcinol and phenol; toluhydroquinone, resorcinol and tetrahydrofurfuryl alcohol; toluhydroquinone, resorcinol, o-cresol or p-cresol or m-cresol; toluhydroquinone, catechol, o-cresol or p-cresol or m-cresol; toluhydroquinone, p-cresol and phenol; toluhydroquinone, resorcinol and dimethylsulfoxide; toluhydroquinone, catechol and dimethylsulfoxide; toluhydroquinone, hydroquinone and dimethylsulfoxide; hydroquinone, catechol and dimethylsulfoxide; hydroquinone, resorcinol and dimethylsulfoxide; catechol, resorcinol and dimethylsulfoxide; toluhydroquinone, resorcinol and dimethyl formamide; toluhydroquinone, catechol and dimethyl formamide; toluhydroquinone, hydroquinone and dimethyl formamide; catechol, hydroquinone and dimethyl formamide; resorcinol, hydroquinone and dimethyl formamide; resorcinol, catechol and dimethyl formamide; hydroquinone, phenol and dimethylsulfoxide; catechol, phenol and dimethylsulfoxide; resorcinol, phenol and dimethylsulfoxide; toluhydroquinone, phenol and dimethylsulfoxide; catechol, phenol and dimethyl formamide; hydroquinone, phenol and dimethyl formamide; resorcinol, phenol and dimethyl formamide; hydroquinone, resorcinol and phenol; catechol, resorcinol and phenol; catechol, hydroquinone and phenol; catechol and dimethylsulfoxide; hydroquinone and dimethylsulfoxide; resorcinol and dimethylsulfoxide; toluhydroquinone and dimethylsulfoxide; phenol and dimethylsulfoxide; catechol and dimethyl formamide; hydroquinone and dimethylformamide; resorcinol and dimethyl formamide; toluhydroquinone and dimethyl formamide; phenol and dimethyl formamide; hydroquinone and benzyl alcohol; resorcinol and benzyl alcohol; resorcinol, phenol and catechol; hydroquinone and phenethyl alcohol; resorcinol and phenethyl alcohol; toluhydroquinone, hydroquinone and p-cresol; catechol, hydroquinone, resorcinol and dimethylsulfoxide; catechol, hydroquinone, resorcinol and dimethyl formamide; and catechol, hydroquinone, resorcinol and p-cresol.

The amounts of extractive solvents employed with the ethyl acetate and methyl ethyl ketone are not necessarily critical. The amounts must be sufficient so that no azeotropes are formed with the ethyl acetate or methyl ethyl ketone or combinations thereof and the relative volatility is greater than 1.20. The amounts of the extractive solvents employed with one part of ethyl acetate (EA) and one part of methyl ethyl ketone (MEK) can range from about 1 part to 5 parts while the amount of each component of the mixtures can range from about ½ part to about 3 parts per each part of EA and MEK.

The following examples will illustrate the invention.

EXAMPLE 1

50 grams of ethyl acetate (EA) and 50 grams of methyl ethyl ketone (MEK) were placed in an Othmer type vapor-liquid equilibrium still and the mixture boiled for eleven hours. Samples of liquid and vapor were then withdrawn and analyzed by gas chromotography. The vapor analyzed 42.4% EA, 57.6% MEK; the liquid analyzed 40.5% EA, 59.5% MEK. This is a relative volatility of EA to MEK of 1.08.

EXAMPLE 2

20 grams ethyl acetate (EA), 20 grams methyl ethyl ketone (MEK) and 60 grams of diacetone alcohol were charged to the same Othmer vapor-liquid equilibrium still used in Example 1 and the mixture boiled for seven hours. Samples of liquid and vapor where then withdrawn and analysis gave vapor comprising 46.9% EA, 53.1% MEK and liquid 41.7% EA, 58.3% MEK. This is a relative volatility of 1.24.

EXAMPLE 3

20 grams ethyl acetate (EA), 20 grams methyl ethyl ketone (MEK), 25 grams phthalic anhydride, 25 grams maleic anhydride and 10 grams diacetone alcohol were charged to the same Othmer vapor-liquid equilibrium still used in Example 1 and the mixture boiled for twelve hours. Samples of liquid and vapor were withdrawn and analysis gave a vapor comprising 45.7% EA, 54.3% MEK and liquid 35.8% EA, 64.2% MEK. This is a relative volatility of 1.51. These examples shown that the relative volatility of EA to MEK can be markedly altered by boiling them in the presence of a third component comprising one or more compounds. This information can now be employed in the following manner to effect more efficiently the separation of EA from MEK in a rectifying column.

EXAMPLE 4

A vacuum jacketed one-inch diameter glass Oldershaw column containing forty actual perforated plates as shown in FIG. 1 was employed. 40 grams ethyl acetate (EA) and 200 grams methyl ethyl ketone (MEK) were introduced into the stillpot and the column operated at 30:1 reflux ratio for one hour. Samples were then withdrawn and analyzed by gas chromatography with the following results: stillpot, 8.4% EA, 91.6% MEK; overhead 24.8% EA, 75.2% MEK. Using a relative volatility of EA to MEK of 1.08 as determined in Example 1, this calibrates the column as having 16.7 theoretical plates.

EXAMPLE 5

To the column and mixture of ethy acetate (EA) and methyl ethyl ketone (MEK) described in Example 4 was pumped diacetone alcohol. The pumping rate was about 7 ml/min, the boil-up rate in the column was about 12.5 ml/min. The reflux ratio was maintained at 30:1 and samples were taken hourly for three hours and analyzed as follows:

| Time | Stillpot | | Overhead | | Theor. Plates | Calculated Rel. Vol. |
|---|---|---|---|---|---|---|
| | % EA | % MEK | % EA | % MEK | | |
| 1st hour | 7.7 | 92.3 | 73.4 | 26.6 | 17 | 1.23 |
| 2nd hour | 6.0 | 94.0 | 77.8 | 22.2 | 17 | 1.265 |
| 3rd hour | 5.5 | 94.5 | 79.7 | 20.3 | 17 | 1.282 |

Examples 4 and 5 show that EA and MEK have a relative volatility of 1.08 when rectified in the conventional way but when it is done in the presence of diacetone alcohol, the relative volatility increases to about 1.28. This is close to the value of 1.24 for diacetone alcohol determined in Example 2. The Othmer vapor-liquid equilibrium still consists of almost exactly one theoretical plate while the Oldershaw column has about 17 theoretical plates under these conditions. The accuracy of the relative volatility is greater when determined in the Oldershaw column. These examples show however that data obtained in the vapor-liquid equilibrium still can be used to predict the performance of extractive distillation agents when used in rectification columns.

EXAMPLES 6-84

Using the vacuum jacket one-inch diameter glass Oldershaw column containing forty actual perforated plates as shown in FIG. 1 and the same procedure as described in Example 3, a number of single compounds as well as mixtures of two or more compounds used as extractive distillation agents were added to the ethyl acetate and methyl ethyl ketone and the mixture boiled for twelve hours at which time samples of the liquid and vapor were withdrawn to determine the relative volatility. The results are presented in Table I. The column headed "ratio" is the weight quantity of the extractive agents employed on a parts basis with one part of the ethyl acetate and one part of methyl ethyl ketone.

TABLE I

EXTRACTIVE DISTILLATION AGENTS USED IN THE SEPARATION OF ETHYL ACETATE FROM METHYL ETHYL KETONE

| Example | Compounds | Ratio | Rel. Vol. |
|---|---|---|---|
| 6 | Maleic anhydride | 2 | 1.37 |
| " | " | 3 | 1.27 |
| 7 | Isophorone | 2 | 1.19 |
| " | " | 3 | 1.25 |
| 8 | Ethylene glycol n-hexyl ether | 2 | 1.15 |
| " | " | 3 | 1.09 |
| 9 | Hexylene glycol | 2 | 1.26 |
| " | " | 3 | 1.21 |
| 10 | Morpholine | 2 | 1.11 |
| " | " | 3 | 1.16 |
| 11 | 2,4-Pentanedione | 2 | 1.18 |
| " | " | 3 | 1.21 |
| 12 | Diacetone alcohol | 2 | 1.33 |
| " | " | 3 | 1.24 |
| 13 | Propylene glycol | 2 | 1.21 |
| " | " | 3 | 1.27 |
| 14 | Phthalic anhydride, Maleic anhydride | 1:1 | 1.31 |
| " | " | 3/2:3/2 | 1.40 |
| 15 | Phthalic anhydride, Isophorone | 1:1 | 1.25 |
| " | " | 3/2:3/2 | 1.26 |
| 16 | Phthalic anhydride, Diacetone alcohol | 1:1 | 1.37 |
| " | " | 3/2:3/2 | 1.28 |
| 17 | Phthalic anhydride, Propylene glycol | 1:1 | 1.32 |
| " | " | 3/2:3/2 | 1.42 |
| 18 | Phthalic anhydride, Propylene glycol | 1:1 | 1.32 |
| " | " | 3/2:3/2 | 1.40 |
| 19 | Phthalic anhydride, Maleic anhydride, Isophorone | 4/5:4/5:2/5 | 1.36 |
| " | " | 5/4:5/4:1/2 | 1.25 |
| 20 | Phthalic anhydride, Maleic anhydride, Diethylmaleate | 4/5:4/5:2/5 | 1.24 |
| " | " | 5/4:5/4:1/2 | 1.30 |
| 21 | Phthalic anhydride, Maleic anhydride, diEt glycol di Me ether | 4/5:4/5:2/5 | 1.30 |
| " | " | 5/4:5/4:1/2 | 1.24 |
| 22 | Phthalic anhydride, Maleic anhydride, Isoborneol | 4/5:4/5:2/5 | 1.25 |
| " | " | 5/4:5/4:1/2 | 1.35 |
| 23 | Phthalic anhydride, Maleic anhydride, di Me succinate | 4/5:4/5:2/5 | 1.22 |
| " | " | 5/4:5/4:1/2 | 1.33 |
| 24 | Phthalic anhydride, Maleic anhydride, Butoxypropanol | 4/5:4/5:2/5 | 1.28 |
| " | " | 5/4:5/4:1/2 | 1.25 |
| 25 | Phthalic anhydride, Maleic anhydride, Dibutyl phthalate | 4/5:4/5:2/5 | 1.28 |
| " | " | 5/4:5/4:1/2 | 1.33 |
| 26 | Phthalic anhydride, Maleic anhydride, Benzophenone | 4/5:4/5:2/5 | 1.29 |
| " | " | 5/4:5/4:1/2 | 1.38 |
| 27 | Phthalic anhydride, Maleic anhydride, Acetophenone | 4/5:4/5:2/5 | 1.27 |
| " | " | 5/4:5/4:1/2 | 1.28 |
| 28 | Phthalic anhydride, Maleic anhydride, Acetol | 4/5:4/5:2/5 | 1.44 |
| " | " | 5/4:5/4:1/2 | 1.53 |
| 29 | Phthalic anhydride, Maleic anhydride, 2-Octanone | 4/5:4/5:2/5 | 1.22 |
| " | " | 5/4:5/4:1/2 | 1.35 |
| 30 | Phthalic anhydride, Maleic anhydride, Diisobutyl Ketone | 4/5:4/5:2/5 | 1.27 |
| " | " | 5/4:5/4:1/2 | 1.29 |
| 31 | Phthalic anhydride, Maleic anhydride, Me isoamyl ketone | 4/5:4/5:2/5 | 1.27 |
| " | " | 5/4:5/4:1/2 | 1.35 |
| 32 | Phthalic anhydride, Maleic anhydride, Diacetone alcohol | 4/5:4/5:2/5 | 1.40 |
| " | " | 5/4:5/4:1/2 | 1.51 |
| 33 | Phthalic anhydride, Maleic anhydride, Et glycol stearate | 4/5:4/5:2/5 | 1.26 |
| " | " | 5/4:5/4:1/2 | 1.24 |
| 34 | Phthalic anhydride, Maleic anhydride, Benzyl alcohol | 4/5:4/5:2/5 | 1.35 |
| " | " | 5/4:5/4:1/2 | 1.44 |
| 35 | Phthalic anhydride, Maleic anhydride, Me—n-amyl ketone | 4/5:4/5:2/5 | 1.27 |
| " | " | 5/4:5/4:1/2 | 1.29 |
| 36 | Phthalic anhydride, Maleic anhydride, Phenethyl alcohol | 4/5:4/5:2/5 | 1.40 |
| " | " | 5/4:5/4:1/2 | 1.42 |
| 37 | Phthalic anhydride, Maleic anhydride, Benzyl benzoate | 4/5:4/5:2/5 | 1.29 |
| " | " | 5/4:5/4:1/2 | 1.16 |
| 38 | Phthalic anhydride, Maleic anhydride, Phenol | 415:4/5:2/5 | 1.34 |

TABLE I-continued
EXTRACTIVE DISTILLATION AGENTS USED IN THE SEPARATION OF ETHYL ACETATE FROM METHYL ETHYL KETONE

| Example | Compounds | Ratio | Rel. Vol. |
|---|---|---|---|
| | " | 5/4:1/2 | 1.32 |
| 39 | Phthalic anhydride, Maleic anhydride, p-Et benzaldehyde | 4/5:4/5:2/5 | 1.19 |
| | " | 5/4:5/4:1/2 | 1.34 |
| 40 | Phthalic anhydride, Maleic anhydride, a-Me benzyl alcohol | 4/5:4/5:2/5 | 1.36 |
| | " | 5/4:5/4:1/2 | 1.48 |
| 41 | Phthalic anhydride, Maleic anhydride, n-Butanol | 4/5:4/5:2/5 | 1.35 |
| | " | 5/4:5/4:1/2 | 1.52 |
| 42 | Phthalic anhydride, Maleic anhydride, Isobutanol | 4/5:4/5:2/5 | 1.30 |
| | " | 5/4:5/4:1/2 | 1.32 |
| 43 | Phthalic anhydride, Maleic anhydride, n-Pentanol | 4/5:4/5:2/5 | 1.29 |
| | " | 5/4:5/4:1/2 | 1.33 |
| 44 | Phthalic anhydride, Maleic anhydride, 2-Me-1-butanol | 4/5:4/5:2/5 | 1.30 |
| | " | 5/4:5/4:1/2 | 1.35 |
| 45 | Phthalic anhydride, Maleic anhydride, Fenchyl alcohol | 4/5:4/5:2/5 | 1.23 |
| | " | 5/4:5/4:1/2 | 1.35 |
| 46 | Phthalic anhydride, Maleic anhydride, 3-Me-1-butanol | 4/5:4/5:2/5 | 1.27 |
| | " | 5/4:5/4:1/2 | 1.35 |
| 47 | Phthalic anhydride, Maleic anhydride, 1-Hexanol | 4/5:4/5:2/5 | 1.37 |
| | " | 5/4:5/4:1/2 | 1.42 |
| 48 | Phthalic anhydride, Maleic anhydride, Cyclohexanol | 4/5:4/5:2/5 | 1.34 |
| | " | 5/4:5/4:1/2 | 1.44 |
| 49 | Phthalic anhydride, Maleic anhydride, Isooctyl alcohol | 4/5:4/5:2/5 | 1.38 |
| | " | 5/4:5/4:1/2 | 1.42 |
| 50 | Phthalic anhydride, Maleic anhydride, Nonyl alcohol | 4/5:4/5:2/5 | 1.29 |
| | " | 5/4:5/4:1/2 | 1.34 |
| 51 | Phthalic anhydride, Maleic anhydride, n-Decanol | 4/5:4/5:2/5 | 1.27 |
| | " | 5/4:5/4:1/2 | 1.32 |
| 52 | Phthalic anhydride, Maleic anhydride, Propionic anhydride | 4/5:4/5:2/5 | 1.27 |
| | " | 5/4:5/4:1/2 | 1.28 |
| 53 | Phthalic anhydride, Maleic anhydride, Nitrobenzene | 4/5:4/5:2/5 | 1.33 |
| | " | 5/4:5/4:1/2 | 1.33 |
| 54 | Phthalic anhydride, Maleic anhydride, Isobornyl acetate | 4/5:4/5:2/5 | 1.28 |
| | " | 5/4:5/4:1/2 | 1.29 |
| 55 | Phthalic anhydride, Maleic anhydride, 2-Ethylbutanol | 4/5:4/5:2/5 | 1.31 |
| | " | 5/4:5/4:1/2 | 1.36 |
| 56 | Phthalic anhydride, Maleic anhydride, Diisobutyl carbinol | 4/5:4/5:2/5 | 1.25 |
| | " | 5/4:5/4:1/2 | 1.24 |
| 57 | Phthalic anhydride, Maleic anhydride, Acetonylacetone | 4/5:4/5:2/5 | 1.46 |
| | " | 5/4:5/4:1/2 | 1.36 |
| 58 | Phthalic anhydride, Maleic anhydride, Et. glycol phenyl ether | 4/5:4/5:2/5 | 1.35 |
| | " | 5/4:5/4:1/2 | 1.45 |
| 59 | Phthalic anhydride, Maleic anhydride, Phenyl acetic acid | 4/5:4/5:2/5 | 1.26 |
| | " | 5/4:5/4:1/2 | 1.41 |
| 60 | Phthalic anhydride, Maleic anhydride, Phenol | 4/5:4/5:2/5 | 1.31 |
| | " | 5/4:5/4:1/2 | 1.44 |
| 61 | Phthalic anhydride, Maleic anhydride, Et. glycol hexyl ether | 4/5:4/5:2/5 | 1.31 |
| | " | 5/4:5/4:1/2 | 1.40 |
| 62 | Phthalic anhydride, Maleic anhydride, Hexylene glycol | 4/5:4/5:2/5 | 1.38 |
| | " | 5/4:5/4:1/2 | 1.44 |
| 63 | Phthalic anhydride, Maleic anhydride, Propoxypropanol | 4/5:4/5:2/5 | 1.34 |
| | " | 5/4:5/4:1/2 | 1.37 |
| 64 | Phthalic anhydride, Maleic anhydride, 1,4-Butanediol | 4/5:4/5:2/5 | 1.34 |
| | " | 5/4:5/4:1/2 | 1.26 |
| 65 | Phthalic anhydride, Maleic anhydride, Propylene glycol | 4/5:4/5:2/5 | 1.52 |
| | " | 5/4:5/4:1/2 | 1.50 |
| 66 | Phthalic anhydride, Maleic anhydride, Benzyl ether | 4/5:4/5:2/5 | 1.29 |
| | " | 5/4:5/4:1/2 | 1.30 |
| 67 | Phthalic anhydride, Maleic anhydride, Benzil | 4/5:4/5:2/5 | 1.30 |
| | " | 5/4:5/4:1/2 | 1.22 |
| 68 | Phthalic anhydride, Maleic anhydride, 2,4-Pentanedione | 4/5:4/5:2/5 | 1.27 |
| | " | 5/4:5/4:1/2 | 1.31 |
| 69 | Phthalic anhydride, Maleic anhydride, Acetoin | 4/5:4/5:2/5 | 1.34 |
| | " | 5/4:5/4:1/2 | 1.54 |
| 70 | Phthalic anhydride, Maleic anhydride, Diethyl carbonate | 4/5:4/5:2/5 | 1.27 |
| | " | 5/4:5/4:1/2 | 1.23 |
| 71 | Phthalic anhydride Maleic anhydride, 2-Methoxyethylacetate | 4/5:4/5:2/5 | 1.23 |
| | " | 5/4:5/4:1/2 | 1.33 |
| 72 | Phthalic anhydride, Maleic anhydride, 2-Nitropropane | 4/5:4/5:2/5 | 1.29 |
| | " | 5/4:5/4:1/2 | 1.36 |
| 73 | Phthalic anhydride, Maleic anhydride, 3-Pentanone | 4/5:4/5:2/5 | 1.15 |
| | " | 5/4:5/4:1/2 | 1.30 |
| 74 | Phthalic anhydride, Maleic anhydride, 1,3-Butylene glycol | 4/5:4/5:2/5 | 1.44 |
| | " | 5/4:5/4:1/2 | 1.35 |
| 75 | Phthalic anhydride, Maleic anhydride, 1,6-Hexanediol | 4/5:4/5:2/5 | 1.39 |
| | " | 5/4:5/4:1/2 | 1.43 |
| 76 | Phthalic anhydride, Maleic anhydride, Neopentyl glycol | 4/5:4/5:2/5 | 1.36 |
| | " | 5/4:5/4:1/2 | 1.24 |
| 77 | Phthalic anhydride, Maleic anhydride, Dipropylene glycol | 4/5:4/5:2/5 | 1.24 |
| | " | f5/4:5/4:1/2 | 1.23 |

TABLE I-continued

EXTRACTIVE DISTILLATION AGENTS USED IN THE SEPARATION OF ETHYL ACETATE FROM METHYL ETHYL KETONE

| Example | Compounds | Ratio | Rel. Vol. |
|---------|-----------|-------|-----------|
| 78 | Phthalic anhydride, Maleic anhydride, Diethylene glycol | 4/5:4/5:2/5 | 1.33 |
| " | | 5/4:5/4:1/2 | 1.44 |
| 79 | Phthalic anhydride, Maleic anhydride, Triethylene glycol | 4/5:4/5:2/5 | 1.37 |
| " | | 5/4:5/4:1/2 | 1.48 |
| 80 | Phthalic anhydride, Maleic anhydride, Tripropylene glycol | 4/5:4/5:2/5 | 1.42 |
| " | | 5/4:5/4:1/2 | 1.32 |
| 81 | Phthalic anhydride, Maleic anhydride, Glycerol | 4/5:4/5:2/5 | 1.37 |
| " | | 5/4:5/4:1/2 | 1.52 |
| 82 | Phthalic anhydride, Maleic anhydride, Isodecanol | 4/5:4/5:2/5 | 1.27 |
| " | | 5/4:5/4:1/2 | 1.32 |
| 83 | Phthalic anhydride, Maleic anhydride, Ethylene glycol | 4/5:4/5:2/5 | 1.38 |
| " | | 5/4:5/4:1/2 | 1.32 |
| 84 | Phthalic anhydride, Maleic anhydride, n-Octanol | 4/5:4/5:2/5 | 1.37 |

Table I lists both individual compounds and combinations of compounds which have been found to enhance the relative volatility of EA to MEK. The degree of enhancement varies widely with the greatest improvement being shown by a mixture of phthalic anhydride, maleic anhydride and propylene glycol.

The advantage of using a mixture instead of the pure compounds is shown in Table II, the data being taken from Table I and rearranged.

TABLE II

| EFFECT OF BLENDS ON RELATIVE VOLATILITY | | |
|---|---|---|
| Compounds | Ratio | Rel. Vol. |
| Phthalic anhydride | Will not dissolve | — |
| Maleic anhydride | 2 | 1.37 |
| " | 3 | 1.27 |
| Propylene glycol | 2 | 1.21 |
| " | 3 | 1.27 |
| Phthalic anhydride, Maleic anhydride | 1:1 | 1.31 |
| " | 3/2:3/2 | 1.40 |
| Phthalic anhydride, Propylene glycol | 1:1 | 1.32 |
| " | 3/2:3/2 | 1.40 |
| Maleic anhydride, Propylene glycol | 1:1 | 1.32 |
| " | 3/2:3/2 | 1.42 |
| Phthalic anhydride, Maleic anhydride, Propylene glycol | 4/5:4/5:2/5 | 1.52 |
| Phthalic anhydride, Maleic anhydride, Propylene glycol | 5/4:5/4:1/2 | 1.50 |
| Diacetone alcohol | 2 | 1.33 |
| " | 3 | 1.24 |
| Phthalic anhydride, Diacetone glycol | 1:1 | 1.25 |
| " | 3/2:3/2 | 1.21 |
| Maleic anhydride, Diacetone alcohol | 1:1 | 1.37 |
| " | 3/2:3/2 | 1.28 |
| Phthalic anhydride, Maleic anhydride, Diacetone alcohol | 4/5:4/5:2/5 | 1.40 |
| Phthalic anhydride, Maleic anhydride Diacetone alcohol | 5/4:54/:1/2 | 1.51 |

Table II shows the advantageous effect of using mixtures of compounds as the extractive distillation agent in separating ethyl acetate from methyl ethyl ketone. Phthalic anhydride alone cannot be used; it does not dissolve in boiling EA-MEK. Maleic anhydride, propylene glycol and diacetone alcohol used singly give relative volatilities in the range 1.21 to 1.37. The combination of phthalic anhydride with diacetone glycol does not improve the relative volatility of EA-MEK compared with diacetone glycol above. When either propylene glycol or diacetone alcohol is added to phthalic anhydride-maleic anhydride, the relative volatility may be increased to 1.5.

To show the reduction in theoretical plate requirements that can be accomplished by increasing the relative volatility, a calculation based on the Fenske equation for columns at total reflux is shown in Table III. This table shows the minimum number of theoretical plates required to separate ethyl acetate from methyl ethyl ketone, both in 99% purity at several different relative volatilities.

TABLE III

MINIMUM NUMBER OF THEORETICAL PLATES REQUIRED FOR 99% PURITY AT SEVERAL RELATIVE VOLATILITIES

| Relative Volatility | No. of Theor. Plates Req'd. |
|---|---|
| 1.08 | 118 |
| 1.10 | 97 |
| 1.20 | 50 |
| 1.30 | 35 |
| 1.40 | 27 |
| 1.50 | 23 |

The data in Table III show that to separate ethyl acetate from methyl ethyl ketone, both compounds in 99% purity, it requires more than 118 theoretical plates in a conventional rectification column. Using extractive distillation to reduce the relative volatility, it requires at least 50 theoretical plates at a relative volatility of 1.2 and at least 23 theoretical plates at a relative volatility of 1.5. Thus the advantage of extractive distillation in this separation becomes apparent. Separations requiring rectification columns consisting of more than a hundred theoretical plates are difficult to operate and control and a marked advantage is obtained by operating with columns in the 20 to 50 theoretical plate range.

EXAMPLES 85–455

Using the vacuum jacketed one-inch diameter glass Odershaw column containing forty actual perforated plates as shown in FIG. 1 and the same procedure as described in Example 3, additional extractive solvents were evaluated for the separation of one part of ethyl acetate and one part of methyl ethyl ketone. Each run comprises the boiling of the mixtures for twelve hours at which time samples of the liquid and vapor were withdrawn to determine the relative volatility. Table IV indicates the relative volatility of ethyl acetate to methyl ethyl ketone obtained using various amounts of extractive agents. The column headed "ratio" is the weight quantity of the extractive agents employed on a parts basis with one part of ethyl acetate and one part of methyl ethyl ketone.

TABLE IV
EXTRACTIVE DISTILLATION AGENTS USED IN THE SEPARATION OF ETHYL ACETATE FROM METHYL ETHYL KETONE

| Example | Compounds | Ratio | Rel. Vol. |
|---|---|---|---|
| 85 | 1-Naphthol | 2 | 1.50 |
| | " | 3 | 1.47 |
| 86 | 1-Naphthol, Catechol | 1:1 | 1.44 |
| | " | 3/2:3/2 | 1.46 |
| 87 | Phenol | 2 | 1.34 |
| | " | 3 | 1.44 |
| 88 | Maleic anhydride, Catechol | (Azeo.) 1:1 | 1.30 |
| | " | 3/2:3/2 | 1.29 |
| 89 | 1-Naphthol, Phenol | 1:1 | 1.44 |
| | " | 3/2:3/2 | 1.39 |
| 90 | 4-tert. Butyl catechol, Phenol | 1:1 | 1.40 |
| | " | 3/2:3/2 | 1.40 |
| 91 | 4-tert. Butyl catechol, 1-Naphthol | 1:1 | 1.38 |
| | " | 3/2:3/2 | 1.28 |
| 92 | 1-Naphthol, o-Cresol | 1:1 | 1.44 |
| | " | 3/2:3/2 | 1.31 |
| 93 | 1-Naphthol, m-Cresol | 1:1 | 1.42 |
| | " | 3/2:3/2 | 1.51 |
| 94 | 1-Naphthol, p-Cresol | 1:1 | 1.41 |
| | " | 3/2:3/2 | 1.38 |
| 95 | 1-Naphthol, Resorcinol | 1:1 | 1.49 |
| | " | 3/2:3/2 | 1.52 |
| 96 | 1-Naphthol, bis Phenol A | 1:1 | 1.49 |
| | " | 3/2:3/2 | 1.58 |
| 97 | 1-Naphthol, Diphenyl ether | 1:1 | 1.35 |
| | " | 3/2:3/2 | 1.40 |
| 98 | bis Phenol A, Catechol | 1:1 | 1.50 |
| | " | 3/2:3/2 | 1.46 |
| 99 | bis Phenol A, 2-Naphthol | 1:1 | 1.53 |
| | " | 3/2:3/2 | 1.40 |
| 100 | 2-Naphthol, Catechol | 1:1 | 1.49 |
| | " | 3/2:3/2 | 1.48 |
| 101 | 2-Naphthol, 1-Naphthol | 1:1 | 1.40 |
| | " | 3/2:3/2 | 1.54 |
| 102 | bis Phenol A, Resorcinol | 1:1 | 1.62 |
| | " | 3/2:3/2 | 1.51 |
| 103 | bis Phenol A, 2-Naphthol | 1:1 | 1.46 |
| | " | 3/2:3/2 | 1.49 |
| 104 | 2-Naphthol, Resorcinol | 1:1 | 1.55 |
| | " | 3/2:3/2 | 1.58 |
| 105 | 2-Naphthol | 2 | 1.43 |
| | " | 3 | 1.42 |
| 106 | Catechol, Pyrogallol | 1:1 | 1.50 |
| | " | 3/2:3/2 | 1.52 |
| 107 | Pyrogallol, 1-Naphthol | 1:1 | 1.49 |
| | " | 3/2:3/2 | 1.52 |
| 108 | Pyrogallol, 2-Naphthol | 1:1 | 1.43 |
| | " | 3/2:3/2 | 1.51 |
| 109 | Catechol, Resorcinol | 1:1 | 1.63 |
| | " | 3/2:3/2 | 1.60 |
| 110 | Resorcinol, o-Cresol | 1:1 | 1.48 |
| | " | 3/2:3/2 | 1.49 |
| 111 | Resorcinol, m-Cresol | 1:1 | 1.61 |
| | " | 3/2:3/2 | 1.54 |
| 112 | Resorcinol, p-Cresol | 1:1 | 1.55 |
| | " | 3/2:3/2 | 1.59 |
| 113 | Resorcinol, Catechol | (Azeo.) 1:1 | 1.45 |
| | " | 3/2:3/2 | 1.47 |
| 114 | Catechol, 2-tert. Butyl phenol | 1:1 | 1.35 |
| | " | 3/2:3/2 | 1.25 |
| 115 | Resorcinol, 3,5-Dimethyl phenol | 1:1 | 1.55 |
| | " | 3/2:3/2 | 1.64 |
| 116 | Resorcinol, 3,4-Dimethyl phenol | 1:1 | 1.48 |
| | " | 3/2:3/2 | 1.53 |
| 117 | Catechol, 3,4-Dimethyl phenol | 1:1 | 1.43 |
| | " | 3/2:3/2 | 1.45 |
| 118 | Catechol, 2,3-Dimethyl phenol | 1:1 | 1.39 |
| | " | 3/2:3/2 | 1.37 |
| 119 | Resorcinol, 2,3-Dimethyl phenol | 1:1 | 1.46 |
| | " | 3/2:3/2 | 1.53 |
| 120 | Catechol, 4-Isopropyl phenol | 1:1 | 1.51 |
| | " | 3/2:3/2 | 1.41 |
| 121 | Resorcinol, 4-Isopropyl phenol | 1:1 | 1.49 |
| | " | 3/2:3/2 | 1.45 |
| 122 | Catechol, 2-Isopropyl phenol | 1:1 | 1.33 |
| | " | 3/2:3/2 | 1.37 |
| 123 | Catechol, 4-tert. Butyl catechol | 1:1 | 1.40 |
| | " | 3/2:3/2 | 1.41 |
| 124 | Resorcinol, 4-tert. Butyl catechol | 1:1 | 1.53 |

TABLE IV-continued
EXTRACTIVE DISTILLATION AGENTS USED IN THE SEPARATION OF ETHYL ACETATE FROM METHYL ETHYL KETONE

| Example | Compounds | Ratio | Rel. Vol. |
|---|---|---|---|
|  | " | 3/2:3/2 | 1.53 |
| 125 | Resorcinol, 2,6-Dimethyl phenol | 1:1 | 1.42 |
|  | " | 3/2:3/2 | 1.45 |
| 126 | Catechol, 2,6-Dimethyl phenol | 1:1 | 1.36 |
|  | " | 3/2:3/2 | 1.34 |
| 127 | Catechol, 4-Ethyl phenol | 1:1 | 1.51 |
|  | " | 3/2:3/2 | 1.35 |
| 128 | Resorcinol, 4-Ethyl phenol | 1:1 | 1.44 |
|  | " | 3/2:3/2 | 1.49 |
| 129 | Resorcinol, 2-n-Butyl-2-ethyl-1,3-propanediol | 1:1 | 1.43 |
|  | " | 3/2:3/2 | 1.30 |
| 130 | Catechol, 2-n-Butyl-2-ethyl-1,3-propanediol | 1:1 | 1.32 |
|  | " | 3/2:3/2 | 1.23 |
| 131 | Catechol, Phenol | 1:1 | 1.47 |
|  | " | 3/2:3/2 | 1.59 |
| 132 | Resorcinol, Phenol | 1:1 | 1.51 |
|  | " | 3/2:3/2 | 1.56 |
| 133 | Hydroquinone, Phenol, Catechol | 1:1:½ | 1.55 |
|  | " | 5/4:3/2:¾ | 1.53 |
| 134 | Catechol, 4-Nitrotoluene | 1:1 | 1.36 |
|  | " | 3/2:3/2 | 1.33 |
| 135 | Hydroquinone, Resorcinol, Catechol | 1:1:2/5 | 1.73 |
|  | " | 5/4:3/2:¾ | 1.66 |
| 136 | Hydroquinone, Resorcinol, Catechol | ¾:¾:¾ | 1.66 |
|  | " | 1:1:1 | 1.53 |
| 137 | Hydroquinone, Resorcinol, Catechol, 1-Naphthol | (¼)⁴ | 1.57 |
|  | " | (⅓)⁴ | 1.53 |
| 138 | Hydroquinone, Resorcinol, Catechol, 2-Naphthol | (¼)⁴ | 1.56 |
|  | " | (⅓)⁴ | 1.61 |
| 139 | Hydroquinone, Resorcinol, Catechol, 1-Naphthol | ¾:¾:¾ | 1.56 |
|  | " | 1:1:1 | 1.59 |
| 140 | Catechol, Resorcinol, 3-Methyl-4-nitrophenol | ¾:¾:¾ | 1.55 |
|  | " | 1:1:1 | 1.55 |
| 141 | Catechol, Resorcinol, Pyrogallol | ¾:¾:¾ | 1.68 |
|  | " | 1:1:1 | 1.59 |
| 142 | Catechol, Pyrogallol | 1:1 | 1.54 |
|  | " | 3/2:3/2 | 1.53 |
| 143 | Catechol, Resorcinol, 4-Ethyl phenol | ¾:¾:¾ | 1.50 |
|  | " | 1:1:1 | 1.52 |
| 144 | Hydroquinone, Catechol, Resorcinol, 4-Et phenol | (¼)⁴ | 1.50 |
|  | " | (⅓)⁴ | 1.46 |
| 145 | Hydroquinone, Catechol, Resorcinol, Pyrogallol | (¼)⁴ | 1.58 |
|  | " | (⅓)⁴ | 1.61 |
| 146 | Resorcinol, Pyrogallol | 1:1 | 1.61 |
|  | " | 3/2:3/2 | 1.44 |
| 147 | Resorcinol, Pyrogallol | (Azeo.) 1:1 | 1.54 |
|  | " | 3/2:3/2 | 1.42 |
| 148 | Catechol, Resorcinol, o-sec. Butyl phenol | ¾:¾:¾ | 1.41 |
|  | " | 4/5:4/5:4/5 | 1.42 |
| 149 | Catechol, Resorcinol, o-tert. Butyl phenol | ¾:¾:¾ | 1.33 |
|  | " | 4/5:4/5:4/5 | 1.46 |
| 150 | Catechol, Resorcinol, 4-tert. Butyl phenol | ¾:¾:¾ | 1.55 |
|  | " | 4/5:4/5:4/5 | 1.45 |
| 151 | Catechol, Resorcinol, 4-Phenylphenol | ¾:¾:¾ | 1.48 |
|  | " | 4/5:4/5:4/5 | 1.52 |
| 152 | Catechol, Resorcinol, 2-Phenylphenol | ¾:¾:¾ | 1.46 |
|  | " | 4/5:4/5:4/5 | 1.45 |
| 153 | m-p-Cresol | 2 | 1.31 |
|  | " | 3 | 1.21 |
| 154 | m-p-Cresol, Catechol | 1:1 | 1.39 |
|  | " | 3/2:3/2 | 1.34 |
| 155 | m-p-Cresol, Resorcinol | 1:1 | 1.57 |
|  | " | 3/2:3/2 | 1.51 |
| 156 | Resorcinol, 4-Ethyl phenol | 1:1 | 1.48 |
|  | " | 3/2:3/2 | 1.55 |
| 157 | HQ, Resorcinol, Catechol, m-p-Cresol | (¼)⁴ | 1.55 |
|  | " | (⅓)⁴ | 1.56 |
| 158 | HQ, Resorcinol, Catechol, 4-Ethylphenol | (¼)⁴ | 1.47 |
|  | " | (⅓)⁴ | 1.52 |
| 159 | HQ, Resorcinol, Catechol, Phenol | (¼)⁴ | 1.57 |
|  | " | (⅓)⁴ | 1.59 |
| 160 | HQ, Resorcinol, Catechol, o-Cresol | (Azeo.) (¼)⁴ | 1.60 |
|  | " | (⅓)⁴ | 1.58 |
| 161 | Catechol, o-Cresol | 1:1 | 1.41 |
|  | " | 3/2:3/2 | 1.36 |
| 162 | HQ, o-Cresol, m-p-Cresol | 1:1:2/5 | 1.47 |
|  | " | 5/4:3/2:3/4 | 1.59 |
| 163 | HQ, Phenol | 1:7/5 | 1.51 |
|  | " | 3/2:2 | 1.51 |

TABLE IV-continued
EXTRACTIVE DISTILLATION AGENTS USED IN THE SEPARATION OF ETHYL ACETATE FROM METHYL ETHYL KETONE

| Example | Compounds | Ratio | Rel. Vol. |
|---|---|---|---|
| 164 | 2,5-Di-tert. butyl hydroquinone, Phenol | 1:7/5 | 1.33 |
| | " | 3/2:2 | 1.32 |
| 165 | Catechol, m-p-Cresol | 1:1 | 1.41 |
| | " | 3/2:3/2 | 1.39 |
| 166 | 4-tert. Butylphenol, m-p-Cresol | 1:1 | 1.31 |
| | " | 3/2:3/2 | 1.31 |
| 167 | 4-tert. Butylcatechol, m-p-Cresol | 1:1 | 1.33 |
| | " | 3/2:3/2 | 1.33 |
| 168 | o-Cresol, m-p-Cresol | ⅔:4/3 | 1.40 |
| | " | 1:2 | 1.37 |
| 169 | Pyrogallol, m-p-Cresol | 1:1 | 1.40 |
| | " | 3/2:3/2 | 1.43 |
| 170 | m-p-Cresol, o-sec. Butyl phenol | 1:1 | 1.34 |
| | " | 3/2:3/2 | 1.27 |
| 171 | m-p-Cresol, o-tert. Butylphenol | 1:1 | 1.42 |
| | " | 3/2:3/2 | 1.47 |
| 172 | o-Cresol, o-tert. Butylphenol | 1:1 | 1.16 |
| | " | 3/2:3/2 | 1.40 |
| 173 | m-p-Cresol, 4-Ethylphenol | 1:1 | 1.36 |
| | " | 3/2:3/2 | 1.32 |
| 174 | o-Cresol, 4-Ethylphenol | 1:1 | 1.31 |
| | " | 3/2:3/2 | 1.25 |
| 175 | Hydroquinone, m-p-Cresol | 4/5:6/5 | 1.45 |
| | " | 5/4:7/4 | 1.45 |
| 176 | Hydroquinone, o-Cresol | 4/5:6/5 | 1.41 |
| | " | 5/4:7/4 | 1.46 |
| 177 | Resorcinol, o-Cresol | 1:1 | 1.45 |
| | " | 3/2:3/2 | 1.52 |
| 178 | Pyrogallol, o-Cresol | 1:1 | 1.35 |
| | " | 3/2:3/2 | 1.39 |
| 179 | o-sec. Butylphenol, o-Cresol | 1:1 | 1.25 |
| | " | 3/2:3/2 | 1.23 |
| 180 | HQ, Resorcinol, Catechol, o-Cresol | (Azeo.) (⅓)$^4$ | 1.45 |
| | " | (⅔)$^4$ | 1.44 |
| 181 | HQ, Resorcinol, Catechol, Pyrogallol | (⅓)$^4$ | 1.55 |
| | " | (⅔)$^4$ | 1.61 |
| 182 | 2,5-Di-tert. butyl HQ, m-p-Cresol, o-Cresol | 1:1:2/5 | 1.34 |
| | " | 5/4:3/2:¾ | 1.28 |
| 183 | HQ, Resorcinol, Pyrogallol | (Azeo.) (⅓)$^4$ | 1.56 |
| | " | (⅔)$^4$ | 1.54 |
| 184 | HQ, Catechol, Pyrogallol | ⅔:⅔:⅔ | 1.57 |
| | " | 1:1:1 | 1.57 |
| 185 | HQ, Resorcinol, Pyrogallol | ⅔:⅔:⅔ | 1.57 |
| | " | 1:1:1 | 1.41 |
| 186 | Resorcinol, Catechol, Pyrogallol | ⅔:⅔:⅔ | 1.46 |
| | " | 1:1:1 | 1.47 |
| 187 | Catechol, Hydroquinone | 1:1 | 1.56 |
| | " | 3/2:3/2 | 1.6- |
| 188 | Hydroquinone, Pyrogallol | 1:1 | 1.63 |
| | " | 3/2:3/2 | 1.57 |
| 189 | Hydroquinone, Resorcinol | 1:1 | 1.52 |
| | " | 3/2:3/2 | 1.58 |
| 190 | Resorcinol, o-sec. Butylphenol | 1:1 | 1.40 |
| | " | 3/2:3/2 | 1.43 |
| 191 | Catechol, o-sec. Butylphenol | 1:1 | 1.38 |
| | " | 3/2:3/2 | 1.41 |
| 192 | Catechol, 4-tert. Amylphenol | 1:1 | 1.37 |
| | " | 3/2:3/2 | 1.35 |
| 193 | Catechol, 4-tert. Butylcatechol | 1:1 | 1.35 |
| | " | 3/2:3/2 | 1.37 |
| 194 | HQ, o-sec. Butylphenol, c-Cresol | 1:1:3/5 | 1.40 |
| | " | 5/4:7/4:3/4 | 1.34 |
| 195 | Hydroquinone, Catechol | (Azeo.) 1:1 | 1.33 |
| | " | 3/2:3/2 | 1.32 |
| 196 | Hydroquinone, Catechol, Pyrogallol | (Azeo.) ⅔:⅔:⅔ | 1.53 |
| | " | 1:1:1 | 1.42 |
| 197 | Catechol, Toluhydroquinone | 1:1 | 1.48 |
| | " | 3/2:3/2 | 1.49 |
| 198 | HQ, Toluhydroquinone, o-Cresol | 1:1:2/5 | 1.48 |
| | " | 1:6/5:3/5 | 1.46 |
| 199 | Catechol, Mono-t-butylhydroquinone | 1:1 | 1.39 |
| | " | 6/5:6/5 | 1.37 |
| 200 | Toluhydroquinone, Mono-t-BuHQ | 1:1 | 1.44 |
| | " | 6/5:6/5 | 1.36 |
| 201 | Toluhydroquinone, Pyrogallol | 1:1 | 1.53 |
| | " | 6/5:6/5 | decomp. |
| 202 | Mono-t-BuHQ, Pyrogallol | 1:1 | 1.35 |
| | " | 6/5:6/5 | 1.27 |
| 203 | Catechol, 4-Nitrotoluene | 1:1 | 1.32 |

TABLE IV-continued
EXTRACTIVE DISTILLATION AGENTS USED IN THE SEPARATION OF ETHYL ACETATE FROM METHYL ETHYL KETONE

| Example | Compounds | Ratio | Rel. Vol. |
|---|---|---|---|
|  | " | 6/5:6/5 | 1.37 |
| 204 | Catechol, 2,5-Di-t. Butyl HQ, o-Cresol | 1:1:2/5 | 1.21 |
|  | " | 1:1:4/5 | 1.21 |
| 205 | Hydroquinone, Resorcinol | 1:1 | 1.58 |
|  | " | 3/2:3/2 | 1.53 |
| 206 | Resorcinol | 2 | 1.55 |
|  | " | 3 | 1.50 |
| 207 | Hydroquinone, hydroquinone monomethyl ether | 7/5:3/5 | 1.36 |
| 208 | " | 7/5:1 | 1.35 |
| 209 | Catechol, hydroquinone monomethyl ether | 1:1 | 1.45 |
| 210 | " | 6/5:6/5 | 1.35 |
| 211 | Resorcinol, hydroquinone monomethyl ether | 1:1 | 1.51 |
| 212 | " | 6/5:6/5 | 1.42 |
| 213 | Catechol, hydroquinone di($\beta$-hydroxyethyl)ether | 1:1 | 1.44 |
| 214 | " | 6/5:6/5 | 1.32 |
| 215 | Resorcinol, hydroquinone di($\beta$-hydroxyethyl)ether | 1:1 | 1.42 |
| 216 | " | 6/5:6/5 | 1.32 |
| 217 | Hydroquinone, hydroquinone di($\beta$-hydroxyethyl)ether and meta and para cersol | 1:1:3/5 | 1.43 |
| 218 | " | 6/5:1:3/5 | 1.24 |
| 219 | Resorcinol, hydroquinone di($\beta$-hydroxyethyl)ether and meta and para cresol | 1:1:3/5 | 1.35 |
| 220 | " | 6/5:1:3/5 | 1.33 |
| 221 | Catechol, 1,4-dimethoxybenzene | 1:1 | 1.23 |
| 222 | " | 6/5:6/5 | 1.25 |
| 223 | Resorcinol, 1,4-dimethoxybenzene | 1:1 | 1.40 |
| 224 | " | 6/5:6/5 | 1.36 |
| 225 | Catechol, p-hydroxyphenylacetic acid | 1:1 | 1.42 |
| 226 | " | 6/5:6/5 | 1.44 |
| 227 | Catechol, chlorohydroquinone | 1:1 | 1.34 |
| 228 | " | 6/5:6/5 | 1.36 |
| 229 | Resorcinol, p-hydroxyphenylacetic acid | 1:1 | 1.47 |
| 230 | " | 6/5:6/5 | 1.47 |
| 231 | Resorcinol, chlorohydroquinone | 1:1 | 1.52 |
| 232 | " | 6/5:6/5 | 1.43 |
| 233 | N—(2-hydroxyethyl)-2-pyrrolidone | 2 | 1.27 |
| 234 | " | 3 | 1.28 |
| 235 | 4,4'-sulfonyldiphenol, dimethylsulfoxide | 1:1 | 1.26 |
| 236 | " | 6/5:6/5 | 1.31 |
| 237 | 4,4'-sulfonyldiphenol, dimethylformamide | 1:1 | 1.26 |
| 238 | " | 6/5:6/5 | 1.31 |
| 239 | Dihydroxydiphenyl sulfone, dimethylsulfoxide | 1:1 | 1.32 |
| 240 | " | 6/5:6/5 | 1.37 |
| 241 | Dihydroxydiphenol sulfone, dimethylformamide | 1:1 | 1.30 |
| 242 | " | 6/5:6/5 | 1.31 |
| 243 | Pentaerythritol, dimethylsulfoxide | 2/3:9/5 | 1.44 |
| 244 | " | 4/5:2 | 1.43 |
| 245 | 4-nitrophenol, meta and para cresol | 1:1 | 1.37 |
| 246 | " | 6/5:6/5 | 1.42 |
| 247 | 4-nitrophenol, nitrobenzene | 1:1 | 1.34 |
| 248 | " | 6/5:6/5 | 1.37 |
| 249 | 4-nitrophenol, 2-nitrotoluene | 1:1 | 1.31 |
| 250 | " | 6/5:6/5 | 1.36 |
| 251 | 4-nitrophenol, 3-nitrotoluene | 1:1 | 1.46 |
| 252 | 4-nitrophenol, ortho-secondary butylphenol | 1:1 | 1.36 |
| 253 | " | 6/5:6/5 | 1.35 |
| 254 | Resorcinol, p-cresol | 1:1 | 1.52 |
| 255 | " | 6/5:6/5 | 1.51 |
| 256 | Catechol, o-tertiary-butylphenol | 1:1 | 1.39 |
| 257 | " | 6/5:6/5 | 1.33 |
| 258 | Catechol, p-cresol | 1:1 | 1.37 |
| 259 | " | 6/5:6/5 | 1.36 |
| 260 | Catechol, hydroquinone, p-cresol | 2/3:2/3:2/3 | 1.53 |
| 261 | " | 4/5:4/5:4/5 | 1.54 |
| 262 | Catechol, resorcinol, p-cresol | 2/3:2/3:2/3 | 1.46 |
| 263 | " | 4/5:4/5:4/5 | 1.41 |
| 264 | Hydroquinone, resorcinol, p-cresol | 2/3:2/3:2/3 | 1.55 |
| 265 | " | 4/5:4/5:4/5 | 1.60 |
| 266 | Toluhydroquinone, p-cresol | 1:1 | 1.40 |
| 267 | " | 6/5:6/5 | 1.39 |
| 268 | Toluhydroquinone, catechol, p-cresol | 2/3:2/3:2/3 | 1.45 |
| 269 | " | 4/5:4/5:4/5 | 1.46 |
| 270 | Toluhydroquinone, resorcinol, p-cresol | 2/3:2/3:2/3 | 1.47 |
| 271 | " | 4/5:4/5:4/5 | 1.46 |
| 272 | Toluhydroquinone, resorcinol, catechol | 2/3:2/3:2/3 | 1.52 |
| 273 | " | 4/5:4/5:4/5 | 1.55 |
| 274 | Toluhydroquinone, resorcinol | 1:1 | 1.52 |
| 275 | " | 6/5:6/5 | 1.47 |
| 276 | Toluhydroquinone | 2 | 1.55 |
| 277 | " | 12:5 | 1.52 |
| 278 | Phenol, p-cresol | 1:1 | 1.35 |

TABLE IV-continued
EXTRACTIVE DISTILLATION AGENTS USED IN THE SEPARATION OF ETHYL ACETATE FROM METHYL ETHYL KETONE

| Example | Compounds | Ratio | Rel. Vol. |
|---|---|---|---|
| 279 | " | 6/5:6/5 | 1.31 |
| 280 | Toluhydroquinone, m-p-cresol, o-tertiary-butylphenol | 2/3:2/3:2/3 | 1.29 |
| 281 | " | 4/5:4/5:4/5 | 1.32 |
| 282 | o-secondary-butylphenol, p-cresol | 1:1 | 1.26 |
| 283 | " | 6/5:6/5 | 1.29 |
| 284 | Phenol, m-p-cresol | 1:1 | 1.44 |
| 285 | " | 6/5:6/5 | 1.32 |
| 286 | Phenol, 2-naphthol | 1:1 | 1.40 |
| 287 | " | 6/5:6/5 | 1.38 |
| 288 | Catechol, hydroquinone, tetrahydrofurfuryl alcohol | 2/3:2/3:2/3 | 1.29 |
| 289 | " | 4/5:4/5:4/5 | 1.32 |
| 290 | Catechol, resorcinol, tetrahydrofurfuryl alcohol | 2/3:2/3:2/3 | 1.42 |
| 291 | " | 4/5:4/5:4/5 | 1.39 |
| 292 | Hydroquinone, resorcinol, tetrahydrofurfuryl alcohol | 2/3:2/3:2/3 | 1.49 |
| 293 | " | 4/5:4/5:4/5 | 1.48 |
| 294 | Catechol, toluhydroquinone, tetrahydrofurfuryl alcohol | 2/3:2/3:2/3 | 1.46 |
| 295 | " | 4/5:4/5:4/5 | 1.36 |
| 296 | Catechol, hydroquinone, benzyl alcohol | 2/3:2/3:2/3 | 1.34 |
| 297 | " | 4/5:4/5:4/5 | 1.44 |
| 298 | Catechol, resorcinol, benzyl alcohol | 2/3:2/3:2/3 | 1.46 |
| 299 | " | 4/5:4/5:4/5 | 1.40 |
| 300 | Hydroquinone, resorcinol, benzyl alcohol | 2/3:2/3:2/3 | 1.54 |
| 301 | " | 4/5:4/5:4/5 | 1.61 |
| 302 | Catechol, hydroquinone, ethyl acetoacetate | 2/3:2/3:2/3 | 1.44 |
| 303 | " | 4/5:4/5:4/5 | 1.37 |
| 304 | Catechol, resorcinol, ethyl acetoacetate | 2/3:2/3:2/3 | 1.44 |
| 305 | " | 4/5:4/5:4/5 | 1.37 |
| 306 | Hydroquinone, resorcinol, ethyl acetoacetate | 2/3:2/3:2/3 | 1.49 |
| 307 | " | 4/5:4/5:4/5 | 1.44 |
| 308 | Hydroquinone, catechol, phenethyl alcohol | 2/3:2/3:2/3 | 1.48 |
| 309 | " | 4/5:4/5:4/5 | 1.48 |
| 310 | Resorcinol, catechol, phenethyl alcohol | 2/3:2/3:2/3 | 1.55 |
| 311 | " | 4/5:4/5:4/5 | 1.36 |
| 312 | Resorcinol, hydroquinone, phenethyl alcohol | 2/3:2/3:2/3 | 1.54 |
| 313 | " | 4/5:4/5:4/5 | 1.50 |
| 314 | Catechol, hydroquinone, ethylphenyl acetate | 2/3:2/3:2/3 | 1.40 |
| 315 | " | 4/5:4/5:4/5 | 1.38 |
| 316 | Catechol, resorcinol, ethylphenyl acetate | 2/3:2/3:2/3 | 1.40 |
| 317 | " | 4/5:4/5:4/5 | 1.38 |
| 318 | Hydroquinone, resorcinol, ethylphenyl acetate | 2/3:2/3:2/3 | 1.47 |
| 319 | " | 4/5:4/5:4/5 | 1.43 |
| 320 | Toluhydroquinone, resorcinol, benzyl alcohol | 2/3:2/3:2/3 | 1.45 |
| 321 | " | 4/5:4/5:4/5 | 1.47 |
| 322 | Toluhydroquinone, resorcinol, phenethyl alcohol | 2/3:2/3:2/3 | 1.55 |
| 323 | " | 4/5:4/5:4/5 | 1.47 |
| 324 | Toluhydroquinone, resorcinol, ethylphenyl acetate | 2/3:2/3:2/3 | 1.40 |
| 325 | " | 4/5:4/5:4/5 | 1.50 |
| 326 | Toluhydroquinone, resorcinol, diethyl maleate | 2/3:2/3:2/3 | 1.41 |
| 327 | " | 4/5:4/5:4/5 | 1.47 |
| 328 | Toluhydroquinone, resorcinol, n-decanol | 2/3:2/3:2/3 | 1.42 |
| 329 | " | 4/5:4/5:4/5 | 1.46 |
| 330 | Toluhydroquinone, resorcinol, phenol | 2/3:2/3:2/3 | 1.44 |
| 331 | " | 4/5:4/5:4/5 | 1.49 |
| 332 | Toluhydroquinone, resorcinol, tetrahydrofurfuryl alcohol | 2/3:2/3:2/3 | 1.44 |
| 333 | " | 4/5:4/5:4/5 | 1.50 |
| 334 | Toluhydroquinone, resorcinol, m-p-cresol | 2/3:2/3:2/3 | 1.54 |
| 335 | " | 4/5:4/5:4/5 | 1.49 |
| 336 | Toluhydroquinone, resorcinol, o-cresol | 2/3:2/3:2/3 | 1.52 |
| 337 | " | 4/5:4/5:4/5 | 1.47 |
| 338 | Toluhydroquinone, resorcinol, m-cresol | 2/3:2/3:2/3 | 1.49 |
| 339 | " | 4/5:4/5:4/5 | 1.46 |
| 340 | Toluhydroquinone, resorcinol, p-cresol | 2/3:2/3:2/3 | 1.52 |
| 341 | " | 4/5:4/5:4/5 | 1.57 |
| 342 | Toluhydroquinone, catechol, m-p-cresol | 2/3:2/3:2/3 | 1.32 |
| 343 | " | 4/5:4/5:4/5 | 1.45 |
| 344 | Toluhydroquinone, catechol, o-cresol | 2/3:2/3:2/3 | 1.42 |
| 345 | " | 4/5:4/5:4/5 | 1.40 |
| 346 | Toluhydroquinone, catechol, m-cresol | 2/3:2/3:2/3 | 1.44 |
| 347 | " | 4/5:4/5:4/5 | 1.37 |
| 348 | Toluhydroquinone, catechol, p-cresol | 2/3:2/3:2/3 | 1.47 |
| 349 | " | 4/5:4/5:4/5 | 1.47 |
| 350 | Toluhydroquinone, resorcinol, p-cresol | (Azeo.) 2/3:2/3:2/3 | 1.42 |
| 351 | " | (Azeo.) 4/5:4/5:4/5 | 1.31 |
| 352 | Toluhydroquinone, p-cresol, phenol | 2/3:2/3:2/3 | 1.40 |
| 353 | " | 4/5:4/5:4/5 | 1.57 |
| 354 | Toluhydroquinone, resorcinol, dimethylsulfoxide | 2/3:2/3:2/3 | 1.49 |
| 355 | " | 4.5:4/5:4/5 | 1.36 |
| 356 | Toluhydroquinone, catechol, dimethylsulfoxide | 2/3:2/3:2/3 | 1.34 |
| 357 | " | 4/5:4/5:4/5 | 1.48 |

TABLE IV-continued
EXTRACTIVE DISTILLATION AGENTS USED IN THE SEPARATION OF ETHYL ACETATE FROM METHYL ETHYL KETONE

| Example | Compounds | Ratio | Rel. Vol. |
|---|---|---|---|
| 358 | Toluhydroquinone, hydroquinone, dimethylsulfoxide | 2/3:2/3:2/3 | 1.53 |
| 359 | " | 4/5:4/5:4/5 | 1.50 |
| 360 | Hydroquinone, catechol, dimethylsulfoxide | 2/3:2/3:2/3 | 1.49 |
| 361 | " | 4/5:4/5:4/5 | 1.47 |
| 362 | Hydroquinone, resorcinol, dimethylsulfoxide | 2/3:2/3:2/3 | 1.49 |
| 363 | " | 4/5:4/5:4/5 | 1.53 |
| 364 | Catechol, resorcinol, dimethylsulfoxide | 2/3:2/3:2/3 | 1.44 |
| 365 | " | 4/5:4/5:4/5 | 1.45 |
| 366 | Toluhydroquinone, resorcinol, dimethylformamide | 2/3:2/3:2/3 | 1.46 |
| 367 | " | 4/5:4/5:4/5 | 1.46 |
| 368 | Toluhydroquinone, catechol, dimethylformamide | 2/3:2/3:2/3 | 1.56 |
| 369 | " | 4/5:4/5:4/5 | 1.48 |
| 370 | Toluhydroquinone, hydroquinone, dimethylformamide | 2/3:2/3:2/3 | 1.48 |
| 371 | " | 4/5:4/5:4/5 | 1.48 |
| 372 | Catechol, hydroquinone, dimethylformamide | 2/3:2/3:2/3 | 1.45 |
| 373 | " | 4/5:4/5:4/5 | 1.48 |
| 374 | Resorcinol, hydroquinone, dimethylformamide | 2/3:2/3:2/3 | 1.48 |
| 375 | " | 4/5:4/5:4/5 | 1.50 |
| 376 | Resorcinol, catechol, dimethylformamide | 2/3:2/3:2/3 | 1.45 |
| 377 | " | 4/5:4/5:4/5 | 1.47 |
| 378 | Hydroquinone, phenol, dimethylsulfoxide | 2/3:2/3:2/3 | 1.55 |
| 379 | " | 4/5:4/5:4/5 | 1.45 |
| 380 | Catechol, phenol, dimethylsulfoxide | 2/3:2/3:2/3 | 1.59 |
| 381 | " | 4/5:4/5:4/5 | 1.41 |
| 382 | Resorcinol, phenol, dimethylsulfoxide | 2/3:2/3:2/3 | 1.51 |
| 383 | " | 4/5:4/5:4/5 | 1.45 |
| 384 | Toluhydroquinone, phenol, dimethylsulfoxide | 2/3:2/3:2/3 | 1.37 |
| 385 | " | 4/5:4/5:4/5 | 1.43 |
| 386 | Catechol, phenol, dimethylformamide | 2/3:2/3:2/3 | 1.35 |
| 387 | " | 4/5:4/5:4/5 | 1.36 |
| 388 | Hydroquinone, phenol, dimethylformamide | 2/3:2/3:2/3 | 1.52 |
| 389 | " | 4/5:4/5:4/5 | 1.34 |
| 390 | Resorcinol, phenol, dimethylformamide | 2/3:2/3:2/3 | 1.51 |
| 391 | " | 4/5:4/5:4/5 | 1.50 |
| 392 | Hydroquinone, resorcinol, phenol | 2/3:2/3:2/3 | 1.43 |
| 393 | " | 4/5:4/5:4/5 | 1.35 |
| 394 | Catechol, resorcinol, phenol | 2/3:2/3:2/3 | 1.49 |
| 395 | " | 4/5:4/5:4/5 | 1.55 |
| 396 | Catechol, hydroquinone, phenol | 2/3:2/3:2/3 | 1.51 |
| 397 | " | 4/5:4/5:4/5 | 1.39 |
| 398 | Catechol, dimethylsulfoxide | 1:1 | 1.41 |
| 399 | " | 6/5:6/5 | 1.30 |
| 400 | Hydroquinone, dimethylsulfoxide | 1:1 | 1.40 |
| 401 | " | 6/5:6/5 | 1.40 |
| 402 | Resorcinol, dimethylsulfoxide | 1:1 | 1.46 |
| 403 | " | 6/5:6/5 | 1.43 |
| 404 | Toluhydroquinone, dimethylsulfoxide | 1:1 | 1.39 |
| 405 | " | 6/5:6/5 | 1.34 |
| 406 | Phenol, dimethylsulfoxide | 1:1 | 1.37 |
| 407 | " | 6/5:6/5 | 1.29 |
| 408 | Catechol, dimethylformamide | 1:1 | 1.31 |
| 409 | " | 6/5:6/5 | 1.31 |
| 410 | Hydroquinone, dimethylformamide | 1:1 | 1.42 |
| 411 | " | 6/5:6/5 | 1.38 |
| 412 | Hydroquinone, dimethylsulfoxide | 2 | 1.27 |
| 413 | " | 12/5 | 1.26 |
| 414 | Resorcinol, dimethylformamide | 1:1 | 1.48 |
| 415 | " | 6/5:6/5 | 1.42 |
| 416 | Toluhydroquinone, dimethylformamide | 1:1 | 1.34 |
| 417 | " | 6/5:6/5 | 1.38 |
| 418 | Phenol, dimethylformamide | 1:1 | 1.33 |
| 419 | " | 6/5:6/5 | 1.30 |
| 420 | Dimethylformamide | 2 | 1.29 |
| 421 | | 12/5 | 1.30 |
| 422 | Resorcinol, phenol, dimethylformamide | (Azeo.) 2/3:2/3:2/3 | 1.37 |
| 423 | " | (Azeo.) 4/5:4/5:4/5 | 1.39 |
| 424 | Resorcinol, phenol, catechol | (Azeo.) 2/3:2/3:2/3 | 1.38 |
| 425 | " | (Azeo.) 4/5:4/5:4/5 | 1.56 |
| 426 | Resorcinol, phenol, dimethylsulfoxide | (Azeo.) 2/3:2/3:2/3 | 1.34 |
| 427 | " | (Azeo.) 4/5:4/5:4/5 | 1.39 |
| 428 | Hydroquinone, resorcinol, benzyl alcohol | (Azeo.) 2/3:2/3:2/3 | 1.36 |
| 429 | " | (Azeo.) 4/5:4/5:4/5 | 1.38 |
| 430 | Hydroquinone, resorcinol, phenethyl alcohol | (Azeo.) 2/3:2/3:2/3 | 1.50 |
| 431 | " | (Azeo.) 4/5:4/5:4/5 | 1.41 |
| 432 | Hydroquinone, benzyl alcohol | 1:1 | 1.42 |
| 433 | " | 6/5:6/5 | 1.34 |
| 434 | Resorcinol, benzyl alcohol | 1:1 | 1.47 |
| 435 | " | 6/5:6/5 | 1.42 |
| 436 | Benzyl alcohol | 2 | 1.19 |

TABLE IV-continued
EXTRACTIVE DISTILLATION AGENTS USED IN THE SEPARATION OF ETHYL ACETATE FROM METHYL ETHYL KETONE

| Example | Compounds | Ratio | Rel. Vol. |
|---|---|---|---|
| 437 | " | 12/5 | 1.20 |
| 438 | Hydroquinone, phenethyl alcohol | 1:1 | 1.42 |
| 439 | " | 6/5:6/5 | 1.43 |
| 440 | Resorcinol, phenethyl alcohol | 1:1 | 1.44 |
| 441 | " | 6/5:6/5 | 1.43 |
| 442 | Phenethyl alcohol | 2 | 1.17 |
| 443 | " | 12/5 | 1.16 |
| 444 | Toluhydroquinone, hydroquinone, p-cresol | 2/3:2/3:2/3 | 1.52 |
| 445 | " | 4/5:4/5:4/5 | 1.52 |
| 446 | Hydroquinone, p-cresol | 1:1 | 1.52 |
| 447 | " | 6/5:6/5 | 1.41 |
| 448 | Catechol, hydroquinone, resorcinol, dimethylsulfoxide | $(1/2)^4$ | 1.49 |
| 449 | " | $(3/4)^4$ | 1.64 |
| 450 | P-cresol, hydroquinone, resorcinol, dimethylsulfoxide | 2 | 1.26 |
| 451 | " | 12/5 | 1.34 |
| 452 | Catechol, hydroquinone, resorcinol, dimethylformamide | $(1/2)^4$ | 1.54 |
| 453 | " | $(3/4)^4$ | 1.58 |
| 454 | Catechol, hydroquinone, resorcinol, p-cresol | $(1/2)^4$ | 1.50 |
| 455 | " | $(3/4)^4$ | 1.50 |

In the ratio where a number such as $(1/2)^4$ is used, this indicates that all components are present in the ratio of 1/2:1/2:1/2:1/2

Table IV describes a few runs marked (Azeo.). This indicates that in these runs the starting mixture was the ethyl acetate-methyl ethyl ketone azeotropes and that the vapor composition in the vapor-liquid equilibrium still was richer in ethyl acetate than the azeotrope. This indicates that these extractive distillation agents or solvents are effective in breaking the azeotrope. Where HQ is used, it represents hydroquinone.

What is claimed is:

1. An improved method for separating ethyl acetate from methyl ethyl ketone which comprises distilling in a substantially anhydrous condition a mixture of ethyl acetate and methyl ethyl ketone in a plate column in the presence of an effective amount of an organic extractive solvent, wherein said extractive solvent:
   (1) is soluble in a boiling ethyl acetate-methyl ethyl ketone mixture;
   (2) does not form an azeotrope with ethyl acetate, methyl ethyl ketone or combinations thereof;
   (3) boils higher than ethyl acetate and methyl ethyl ketone; and
   (4) in combination with ethyl acetate-methyl ethyl ketone, results in a relative volatility of ethyl acetate to methyl ethyl ketone greater than 1.20.

2. The process of claim 1 wherein the extractive solvent in combination with ethyl acetate-methyl ethyl ketone results in a relative volatility of ethyl acetate to methyl ethyl ketone in the range from about 1.30 to 1.75.

3. The process of claim 2 wherein the extractive solvent in combination with ethyl acetate-methyl ethyl ketone results in a relative volatility of ethyl acetate to methyl ethyl ketone in the range from about 1.30 to about 1.50.

4. The process of claim 1 wherein the extractive solvent is selected from a member of the group consisting of maleic anhydride, catechol, m- and p-cresol, o-cresol, 2-naphthol, 1-naphthol, phenol, resorcinol, isophorone, propylene glycol, diacetone alcohol, hexylene glycol, neopentyl glycol, dimethylsulfoxide, dimethylformamide, N-(2-hydroxyethyl)-2-pyrrolidone and toluhydroquinone.

5. The process of claim 1 wherein the extractive solvent is a mixture of phthalic anhydride and a compound selected from the group consisting of maleic anhydride, isophorone, propylene glycol and diacetone alcohol.

6. The process of claim 1 wherein the extractive solvent is a mixture of maleic anhydride and a compound selected from the group consisting of catechol, diacetone alcohol and propylene glycol.

7. The process of claim 1 wherein the extractive solvent is a mixture of phthalic anhydride, maleic anhydride and a compound selected from the group consisting of iosphorone, diethyl maleate, the combination of diethylene glycol and dimethyl ether, isoborneol, dimethyl succinate, butoxypropanol, dibutyl phthalate, benzophenone, acetophenone, acetol, 2-octanone, diisobutyl ketone, methyl isoamyl ketone, diacetone alcohol, ethylene glycol stearate, benzyl alcohol, methyl-n-amyl ketone, phenethyl alcohol, benzyl benzoate, phenol, p-ethylbenzaldehyde, α-methyl benzyl alcohol, n-butanol, n-pentanol, 2-methyl-1-butanol, fenchyl alcohol, 3-methyl-1-butanol, 1-hexanol, cyclohexanol, isooctyl alcohol, nonyl alcohol, n-decanol, propionic anhydride, nitrobenzene, isobornyl acetate, 2-ethylbutanol, diisobutyl carbinol, acetonylacetone, ethylene glycol phenyl ether, phenyl acetic acid, ethylene glycol hexyl ether, hexylene glycol, propoxypropanol, 1,4-butanediol, propylene glycol, benzyl ether, benzil, 2,4-pentanedione, acetoin, diethyl carbonate, 2-methyoxyethylacetate, 2-nitropropane, 3-pentanone, 1,3-butylene glycol, 1,6-hexanediol, neopentyl glycol, dipropylene glycol, diethylene glycol, triethylene glycol, tripropylene glycol, glycerol, isodecanol, ethylene glycol and n-octanol.

8. The process of claim 1 wherein the extractive solvent is selected from the mixtures consisting of 1-naphthol and catechol; 1-naphthol and phenol; 1-naphthol and 4-t-butylcatechol; 1-naphthol and o-cresol; 1-naphthol and m-cresol; 1-naphthol and p-cresol; 1-naphthol and resorcinol; 1-naphthol and bis Phenol A; 1-naphthol and diphenyl ether; 1-naphthol and 2-naphthol; 1-naphthol and pyrogallol; 4-t-butyl catechol and phenol; bis Phenol A and catechol; bis Phenol A and 2-naphthol; 2-naphthol and catechol; bis Phenol A and resorcinol; 2-naphthol and resorcinol; catechol and pyrogallol; pyrogallol and 2-naphthol; catechol and resorcinol; resorcinol with each individually o-cresol, m-cresol, and p-cresol; catechol and 2-t-butylphenol; resorcinol and 3,5-dimethylphenol; resorcinol and 3,4-dimethylphenol; catechol and 3,4-dimethylphenol; catechol and 2,3-dimethylphenol; resorcinol and 2,3-dimethylphenol; catechol and 4-isopropyl phenol; resorcinol and 4-isopropylphenol; catechol and 2-isopropylphenol; catechol and 4-t-butylcatechol; resorcinol and 4-t-butylcatechol; resorcinol and 2,6-dimethylphenol; catechol and 2,6-dimethylphenol; catechol and 4-ethylphenol; resorcinol and 2n-butyl-2-ethyl-1-3-propanediol; resorcinol and 4-ethylphenol; catechol and 2-n-butyl-2-ethyl-1,3-propanediol; catechol and phenol; resorcinol and phenol; hydroquinone, phenol and catechol; catechol and 4-nitrotoluene; hydroquinone, resorcinol and catechol; hydroquinone, resorcinol, catechol and 2-naphthol; hydroquinone, resorcinol, catechol and 1-naphthol; hydroquinone, resorcinol and 1-naphthol; catechol, resorcinol and 3-methyl-4-nitrophenol; catechol, resorcinol and pyrogallol; catechol and pyrogallol; catechol, resorcinol and 4-ethylphenol; hydroquinone, catechol, resorcinol and 4-ethylphenol; hydroquinone, catechol, resorcinol and pyrogallol; resorcinol and pyrogallol; catechol, resorcinol and o-sec butyl phenol or o-t-butyl phenol or 4-t-butyl phenol; catechol, resorcinol and 4-phenylphenol or 2-phenylphenol; m-p-cresol and catechol; m-p-cresol and resorcinol; resorcinol and 4-ethylphenol; hydroquinone, resorcinol, catechol and m-p-cresol or 4-ethylphenol or phenol or o-cresol; catechol and o-cresol; hydroquinone, o-cresol and m-p-cresol; hydroquinone and phenol; 2,5-di-t-butylhydroquinone and phenol; catechol and m-p-cresol; 4-t-butylphenol and m-p-cresol; 4-t-butylcatechol and m-p-cresol; o-cresol and m-p-cresol; pyrogallol and m-p-cresol; m-p-cresol and o-sec-butylphenol or o-t-butylphenol; o-cresol and o-t-butylphenol; m-p-cresol and 4-ethylphenol; o-cresol and 4-ethylphenol; hydroquinone and m-p-cresol; hydroquinone and o-cresol; resorcinol and o-cresol; pyrogallol and o-cresol; o-sec butylphenol and o-cresol; hydroquinone, resorcinol, catechol and o-cresol; hydroquinone, resorcinol, catechol and pyrogallol; 2,5-di-t-butyl hydroquinone, m-p-cresol and o-cresol; hydroquinone, resorcinol, catechol and pyrogallol; hydroquinone, catechol and pyrogallol; hydroquinone, resorcinol and pyrogallol; resorcinol, catechol and pyrogallol; catechol and hydroquinone, hydroquinone and pyrogallol; hydroquinone and resorcinol; resorcinol and o-sec butylphenol; catechol and o-sec butylphenol; catechol and 4-t-amylphenol; catechol and 4-t-butylcatechol; hydroquinone, o-sec butylphenol and o-cresol; hydroquinone and catechol; hydroquinone, catechol and pyrogallol; catechol and toluhydroquinone; hydroquinone, toluhydroquinone and o-cresol; catechol and mono-t-butylhydroquinone; toluhydroquinone and pyrogallol; mono-t-butylhydroquinone and pyrogallol; catechol and 4-nitrotoluene; catechol, 2,5-di-t-butylhydroquinone and o-cresol; hydroquinone and resorcinol; hydroquinone and hydroquinone monomethyl ether; catechol and hydroquinone monomethyl ether; resorcinol and hydroquinone mnomethyl ether; catechol and hydroquinone di(β-hydroxyethyl)ether; resorcinol and hydroquinone di(β-hydroxyethyl)ether; hydroquinone, hydroquinone di(β-hydroxyethyl)ether and meta- and para-cresol; resorcinol, hydroquinone di(β-hydroxyethyl)ether and meta- and para-cresol; catechol and 1,4-dimethyoxybenzene; resorcinol and 1,4-dimethoxybenzene; catechol and p-hydroxyphenyl acetic acid; catechol and chlorohydroquinone; resorcinol and p-hydroxyphenyl acetic acid; 4,4'-sulfonyl diphenol and dimethylsulfoxide; dihydroxydiphenyl sulfone and dimethylsulfoxide, 4,4'-sulfonyl diphenol and dimethyl formamide; dihydroxydiphenyl sulfone and dimethyl formamide; pentaerythritol and dimethylsulfoxide; 4-nitrophenol and meta- and para-cresol; 4-nitrophenol and meta- and para-cresol; catechol and o-tetiary-butylphenol; catechol and p-cresol; catechol, hydroquinone and p-cresol; catechol, resorcinol and p-cresol; toluhydroquinone and p-cresol; toluhydroquinone, catechol and p-cresol; toluhydroquinone, resorcinol and p-cresol; toluhydroquinone, resorcinol and catechol; toluhydroquinone and resorcinol; phenol and p-cresol; toluhydroquinone, m-p-cresol, o-tertiary-butylphenol; o-sec butylphenol and p-cresol; phenol and 2-naphthol; catechol, hydroquinone and tetrahydrofurfuryl alcohol; catechol, resorcinol and tetrahydrofurfuryl alcohol; hydroquinone, resorcinol and tetrahydrofurfuryl alcohol, catechol, toluhydroquinone and tetrahydrofurfuryl alcohol; catechol, hydroquinone and benzyl alcohol; catechol, resorcinol and benzyl alcohol; hydroquinone, resorcinol and benzyl alcohol; catechol, hydroquinone and ethyl acetoacetate; catechol, resorcinol and ethyl acetoacetate; hydroquinone, resorcinol and ethyl acetoacetate; hydroquinone, catechol and phenethyl alcohol; resorcinol, catechol and phenethyl alcohol; resorcinol, hydroquinone and phenethyl alcohol; catechol, hydroquinone and ethylphenyl acetate; catechol resorcinol and ethylphenyl acetate; hydroquinone, resorcinol and ethylphenyl acetate; toluhydroquinone, resorcinol and benzyl alcohol; toluhydroquinone, resorcinol and phenethyl alcohol; toluhydroquinone, resorcinol and ethylphenyl acetate; toluhydroquinone, resorcinol and diethyl maleate; toluhydroquinone, resorcinol and n-decanol; toluhydroquinone, resorcinol and phenol; toluhydroquinone, resorcinol and tetrahydrofurfuryl alcohol; toluhydroquinone, resorcinol, o-cresol or p-cresol or m-cresol; toluhydroquinone, catechol, o-cresol or p-cresol or m-cresol; toluhydroquinone, p-cresol and phenol; toluhydroquinone, resorcinol and dimethylsulfoxide; toluhydroquinone, catechol and dimethylsulfoxide; toluhydroquinone, hydroquinone and dimethylsulfoxide; hydroquinone, catechol and dimethylsulfoxide; hydroquinone, resorcinol and dimethylsulfoxide; catechol, resorcinol and dimethylsulfoxide; toluhydroquinone, resorcinol and dimethyl formamide; toluhydroquinone, catechol and dimethyl formamide; toluhydroquinone, hydroquinone and dimethyl formamide; catechol, hydroquinone and dimethyl formamide; resorcinol, hydroquinone and dimethyl formamide; resorcinol, catechol and dimethyl formamide; hydroquinone, phenol and diemthylsulfoxide; catechol, phenol and dimethylsulfoxide; resorcinol, phenol and dimethylsulfoxide; toluhydroquinone, phenol and dimethylsulfoxide; catechol, phenol and dimethyl formamide; hydroquinone, phenol and dimethyl formamide; resorcinol, phenol and dimethyl formamide; hydroquinone, resorcinol and phenol; catechol, resorcinol and phenol; catechol, hydroquinone and phenol; catechol and dimethylsulfoxide; hydroquinone and dimethylsulfoxide; resorcinol and dimethylsulfoxide; toluhydroquinone and dimethylsulfoxide; phenol and dimethylsulfoxide; catechol and dimethyl formamide; hydroquinone and dimethylformamide; resorcinol and dimethyl formamide; toluhydroquinone and dimethyl formamide; phenol and dimethyl formamide; hydroquinone and benzyl alcohol; resorcinol and benzyl alcohol; resorcinol, phenol and catechol, hydroquinone and phenethyl alcohol; resorcinol and phenethyl alcohol; toluhydroquinone, hydroquinone and p-cresol; hydroquinone and p-cresol; catechol, hydroquinone, resorcinol and dimethylsulfoxide; catechol, hydroquinone, resorcinol and dimethyl formamide; and catechol, hydroquinone, resorcinol and p-cresol.

* * * * *